(12) United States Patent
Lidestri (10) Patent No.: US 9,597,529 B2
(45) Date of Patent: Mar. 21, 2017

(54) RAPID RANGE STACKING (RRS) FOR PARTICLE BEAM THERAPY

(75) Inventor: Joseph Lidestri, New York, NY (US)

(73) Assignee: Best Medical International, Inc., Springfield, VA (US)

( * ) Notice: Subject to any disclaimer, the term of this patent is extended or adjusted under 35 U.S.C. 154(b) by 788 days.

(21) Appl. No.: 13/604,415

(22) Filed: Sep. 5, 2012

(65) Prior Publication Data

US 2012/0330086 A1 Dec. 27, 2012

(51) Int. Cl.
*A61N 5/10* (2006.01)

(52) U.S. Cl.
CPC .... *A61N 5/1043* (2013.01); *A61N 2005/1087* (2013.01)

(58) Field of Classification Search
CPC .... A61N 5/103; A61N 5/1031; A61N 5/1038; A61N 5/1043; A61N 2005/1087; A61N 2005/1034; A61N 2005/1041
USPC ............ 600/1–8; 250/492.22, 492.23, 492.3, 250/492.2, 492.1
See application file for complete search history.

(56) References Cited

U.S. PATENT DOCUMENTS

| | | | |
|---|---|---|---|
| 2005/0020917 A1* | 1/2005 | Scherch | 600/437 |
| 2010/0008466 A1* | 1/2010 | Balakin | 378/62 |
| 2010/0127185 A1* | 5/2010 | Fragner et al. | 250/398 |
| 2012/0241635 A1* | 9/2012 | Luechtenborg et al. | 250/389 |

OTHER PUBLICATIONS

"Synchrotron delivers full spectrum of ions", MedicalPhysicsWeb, May 4, 2012, 3 pages.
"Brookhaven Physicists Team Up with Medical Industry to Build Advanced Cancer Therapy Accelerator", BNL Newsroom, Feb. 27, 2012, 3 pages.
"Lattice Design of a Rapid Cycling Medical Synchrotron for Carbon/Proton Therapy", D. Trbojevic et al., Proceedings of IPAC2011, San Sebastian, Spain, 2011, pp. 2541-2543.

* cited by examiner

*Primary Examiner* — Samuel Gilbert (57) ABSTRACT

A rapid range stacking for particle beam therapy includes a position and tracking module used for a patient position and locating a region of interest, and a scanning routine module used for targeting a target voxel within the region of interest by accessing a treatment plan characterization while providing a prescribed amount of dose to the target voxel. The scanning routine module determines a prescribed amount of dose for the target voxel by incrementing a position location of horizontal indexes on a single vertical index. Further, a beam delivery module used for controlling a beam device delivers ion particles to the target voxel within the region of interest. The beam delivery module controls a power supply for a horizontal magnet and a vertical magnet by retrieving information from the scanning routine module, and also controls a power supply for an accelerator energy selection.

20 Claims, 7 Drawing Sheets

RAPID RANGE STACKING (RRS) FOR PARTICLE BEAM THERAPY

FIELD OF THE INVENTION

The present invention relates to a method for delivering actively scanned pencil beams combined with dynamic longitudinal scanning for use in particle beam radiation for therapeutic applications. More specifically, the present invention relates to the delivery of charged particle beams of various species generated from a Rapid Cycling Synchrotron (RCS) or similar device to treat deep-seated cancer and noncancerous lesions.

BACKGROUND

Modern day radiation therapy (RT) of tumors can involve optimizing a target dose escalation for healthy tissue dose reduction and dose fractionation. It is known in the art that tumors can be eradicated if a sufficient dose is delivered to the tumor volume. However, complications may result from use of the necessary effective radiation dose, such as damage to healthy tissue which surrounds the tumor, or to other healthy body organs located close to the tumor. A goal of conformal radiation therapy is to confine the delivered radiation dose to only the tumor volume defined by the margins of the tumor, while minimizing the dose of radiation to surrounding healthy tissue or adjacent healthy organs.

In conventional radiation therapy with x-rays, intensity modulating radiation therapy (IMRT) offers an effective treatment for certain types of tumors and deep-seated lesions when a sufficient radiation dose is delivered. Cancer cells are often more sensitive to radiation damage than is surrounding healthy tissue due to inefficient repair. IMRT is delivered by external source of radiation from either a gamma emitter or linear accelerator.

The linear accelerator typically has a radiation beam source which is rotated about the patient and directs the radiation beam toward the tumor to be treated. The beam intensity of the radiation beam is predetermined and optimized for all azimuthal rotation angles. Multileaf collimators, which have multiple leaf, or finger, projections which can be moved individually into and out of the path of the radiation beam, can be programmed to follow the spatial contour of the tumor as seen by the radiation beam as it passes through the tumor, or the "beam's eye view" of the tumor during the rotation of the radiation beam source, which is mounted on a rotatable gantry of the linear accelerator. The multiple leaves of the multileaf collimator form an outline of the tumor shape as presented by the tumor volume in the direction of the path of travel of the radiation beam, and thus block the transmission of radiation to tissue disposed outside the tumor's spatial outline as presented to the radiation beam, dependent upon the beam's particular azimuthal orientation with respect to the tumor volume.

Tumors that are located deep within the body are generally not amenable to internal forms of treatment. The intrinsic nature of conventional radiation therapy with x-rays always includes damage to healthy tissue as it enters and exits the tumor volume and conformity is limited to the superposition of intersecting beams.

Figure 1:
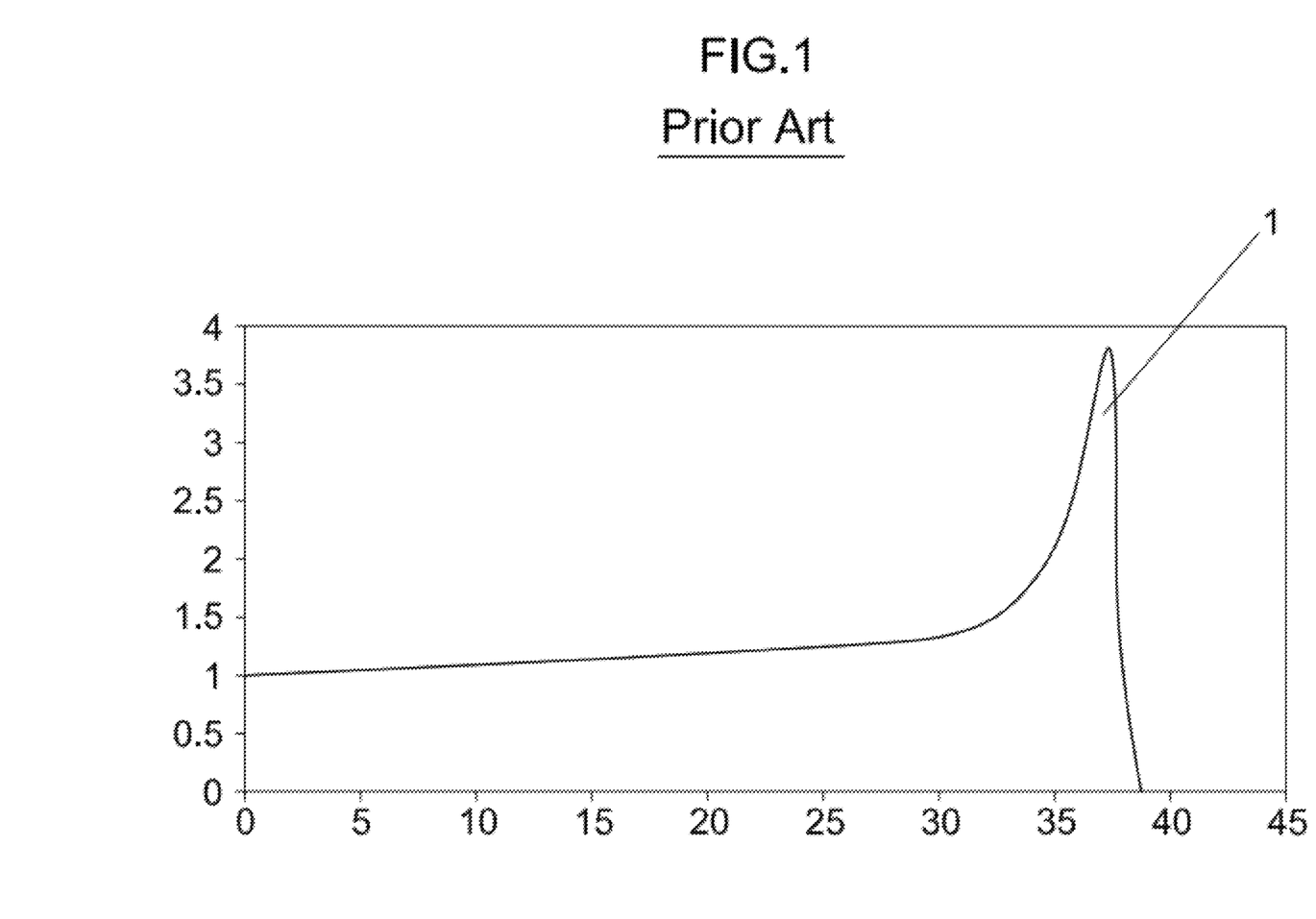
FIG. 1 is a prior art illustration of a sample Bragg peak for a proton released from a cyclotron or synchrotron.

Another form of external beam radiotherapy is intensity modulated particle therapy (IMPT), which relies on the ballistic nature of particles to produce an inverse depth dose. Particle therapy typically utilizes an accelerator to generate high-energy protons to deposit dose in its path to a tumor before stopping at a precise depth known as its range. Particles heavier then protons, such as carbon ions, are additionally used to take advantage of higher linear energy transfer (LET) in causing more effective biological damage. Specifically, the charged particles damage the DNA within the cells, reducing the reproduction of the cell. The higher mass particles, such as carbon ions, can produce more DNA damage per unit of physical dose. This effect is characterized as relative biological effectiveness (RBE). Further, the larger mass associated with heavy ions, such as carbon, are characterized by reduced coulombic multiple scattering and range strangling. This can result in high spatial precision given the reduced lateral beam widening and sharper distal fall off in the tissue outside the tumor volume. The great advantage of particles, either protons or heavier ions, is the energy level stops, and thus, they do not produce an exit dose in the patient. This can result in reduction of side effects to surrounding tissue. All particles have a variety of energy levels that determines the depth of treatment of the tumor. Delivered to the tissue is a maximum deposition of energy just over the last few millimeters of the particles range called the Bragg peak. The Bragg peak is an inverse dose distribution level as shown in FIG. 1. The Bragg peak, indicated as reference number 1 in FIG. 1, demonstrates a low level of energy. As the particles are entering the human body, there is an increase in energy at a specific depth, which can be the region of interest. Thus, the high peak of energy should be within the tumor. This allows minimal damage to the surrounding tissue as compared to the actual tumor.

IMRT and IMPT can have positive and negative affects to the patient. IMPT takes advantage of both biological and physical effects. The first is for disease sites that favor the delivery of higher RBE radiation. Second, those treatments where the increased precision of particle therapy is used to reduce unwanted side effects by limiting the dose to normal tissue. In IMPT, the particle distributes high amounts of energy at a specific distance and then has minimal damage to the normal tissue. As opposed to IMRT which may deliver a high level of energy prior to entering into the tissue. Further, depending on the particle mass, IMPT can produce a narrower pencil beam, as opposed to conventional IMRT.

Currently, IMPT is delivered with passive double scattering and active scanning techniques. Double passive scattering is the most common technique that delivers a broad beam that must be adjusted with patient-specific hardware that shapes the beam to conform to the shape of the tumor. Passive double scattering, although still the most widely used technique, is being replaced with a process called active scanning or more commonly called pencil beam scanning ("PBS") because of the correlation to the optimization algorithm for calculating dose in treatment planning systems ("TPS"). PBS was first introduced by T. Kanai et al. in 1980 and was developed at the Paul Scherer Institute in the mid 1990's. PBS delivers a much more precise beam and has superior 3D dose conformity as compared to passive double scattering.

Figure 2:
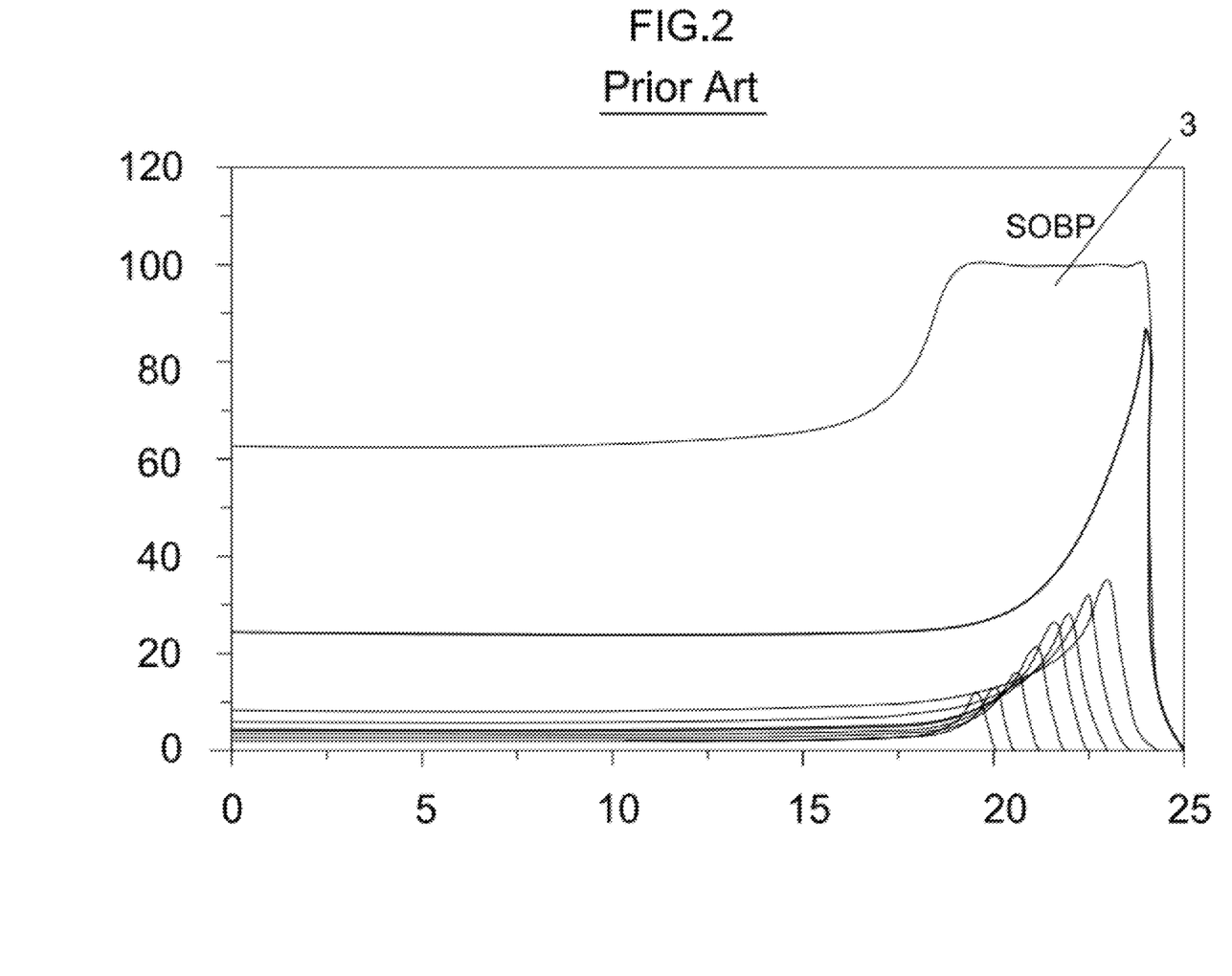
FIG. 2 is prior art illustration of a Spread Out Bragg Peak (SOBP) for a plurality of protons released from a cyclotron or synchrotron.

In addition, there is the Spread Out Bragg Peaks, as indicated as reference number 3 as illustrated in FIG. 2. The Spread Out Bragg Peak (SOBP) can be used to demonstrate that particle therapy can distribute evenly throughout a tumor by superimposing multiple beams at varying energy. Currently, there are no known methods to deliver an entire SOBP dynamically. Further, there are fundamentally many inaccuracies when producing an SOBP sequentially for one energy per transverse scan.

Therefore, one of ordinary skill in the art can appreciate a need to precisely balance against the competing objective of destroying as much of the cancerous tissue as possible and in reducing exposure to healthy tissue. Thus, the objective is to deliver a dose sufficient to eradicate or dramatically reduce the tumor while minimizing the impact on surrounding normal tissue.

High-energy particles can be precisely formed into individual beams described as a pencil beam with spatial and angular dimensions. Charged particles, such as protons and carbon ions are characterized with inverse depth dose curves that have a specific range associated with particle kinetic energy. This unique dosimetric characteristic provides the $3^{rd}$ dimension in producing a uniform dose volume with the ability to generate particles at specific energies corresponding to precise penetration depths (z-axis). This $3^{rd}$ longitudinal dimension, when combined with the two transverse planes in the x-axis and the y-axis, requires scanning each pencil beam along the three axes (x-y-z). Each pencil beam is composed of an individual pristine Bragg peak that needs to be scanned in two orthogonal transverse (x-y) planes and one longitudinal z-axis. The pencil beam is physically repositioned for each transverse (x-y) position, while the longitudinal z-axis corresponds to the depth of the tumor and requires the generation of Bragg peaks of different energies, one for each depth. To create a uniform dose with depth, many pristine Bragg peaks are layered (stacked) one energy level per transverse scan cycle. A Spread Out Bragg Peak (SOBP), shown in FIG. 2, is typically generated after many transverse scan cycles and results in a uniform dose along the tumor depth. A dose distribution can be delivered conformal to a tumor volume of arbitrary shape using multiple pencil beams. The precision in conforming to the tumor volume is optimized by using pencil beams as small as possible. Therefore, a large number of pencil beams are required. A 3D volume can be decomposed into 3D pixels called voxels. For example, a 1 liter-cubic tumor volume would require over 1,000 x-y transverse positions and 62 energy steps (layers) for carbon ions, resulting in 68,000 individual voxels.

Therefore, one of ordinary skill in the art would appreciate a method of delivering ion radiation to a patient in fewer volumetric steps by reducing the scanning of the x-coordinate and y-coordinate, which causes latencies between scanning and delivering dose.

SUMMARY OF INVENTION

According to one general aspect there is provided an apparatus for delivering a longitudinal column of dose rapidly to depth extrema of a tumor. The apparatus includes a position and tracking module used for a patient position and also locating a region of interest. The position and tracking module includes a registration, verification used in conjunction with a patient motion sensor and a tumor motion sensor to determine the exact location of a target voxel. Further, the apparatus includes a scanning routine module used for targeting the target voxel within the region of interest by accessing a treatment plan characterization while providing a prescribed amount of dose to the target voxel. The scanning routine module determines a prescribed amount of dose for the target voxel in a horizontal index and a single vertical index. Additionally, the apparatus includes a beam delivery module used for controlling a beam device that delivers ion particles to the target voxel within the region of interest. The beam delivery module controls a power supply for a horizontal magnet and a vertical magnet by retrieving information from the scanning routine module. The beam delivery module also controls a power supply for an accelerator energy selection that is connected to the beam device. Further, the beam delivery module reads a horizontal strip detector and a vertical strip detector to detect a transverse position. Furthermore, the tumor motion sensor and the patient motion sensor are connected to a timing module, where the tumor motion sensor tracks the region of interest. Furthermore, the timing module is connected to a decision controller that selects a static delivery or a dynamic delivery. The static delivery contains a static time stamp and uses treatment planning data used by the scanning routine module. The dynamic delivery would contain adaptive treatment planning data accessed by the scanning routine module. Furthermore, the timing module is connected to a beam delivery gate that is used by the beam delivery module. Furthermore, the scanning routine module further includes a database treatment planning system that is associated with the beam delivery module and the position and tracking module. Furthermore, the scanning routine module retrieves from the database treatment planning system a dose prescription, a position location, a position time for a specific voxel, and a flag for dose delivery of the region of interest. Furthermore, the scanning routine module initiates a delivery beam to the beam delivery module to begin delivery of the dose prescription and to trigger a stop beam. Furthermore, the scanning routine module determines the prescribed dose prescription for one or more target voxels corresponding to data points at a corresponding depth for one or more stacks of voxels of an energy deposition array for the region of interest, each of the data points corresponding to a horizontal index and a vertical index at an associated depth in an energy deposition array. Also, the scanning routine module increments from the position location of a horizontal index to a position location of another horizontal index on a corresponding single vertical index in the energy deposition array after a dose prescription determined for each target voxel of a corresponding stack of voxels of a horizontal index on the corresponding single vertical index has been delivered. If the energy deposition array has at least one other vertical index in the region of interest, similarly for each vertical index in the region of interest in the energy deposition array, the scanning routine module determines a dose prescription for each target voxel at a corresponding data point at a corresponding depth in a corresponding stack of voxels by incrementing to another vertical index in the energy deposition array and to a position of a horizontal index on the corresponding incremented single vertical index in the energy deposition array until a dose prescription determined for each target voxel at each corresponding data point of each horizontal index on the corresponding incremented single vertical index has been delivered for each such incremented vertical index. The scanning routine module therefore determines a dose prescription for each target voxel of the stacks of voxels at a corresponding depth in the energy deposition array by incrementing the position location of a vertical index until the determined dose prescription has been delivered to target voxels for the vertical indexes and corresponding horizontal indexes in the energy deposition array. Furthermore, the beam delivery module further includes a beam control interface that is connected to a horizontal power supply and a vertical power supply. The beam delivery module further includes the beam control interface that is connected to an accelerator energy selection power source and accelerator beam intensity control power source. Furthermore, the horizontal power supply is connected to the horizontal magnet and a magnetic field sensor H and the vertical power supply is connected to the vertical magnet and a magnetic field sensor V. Furthermore, the accelerator energy selection power source is connected to a beam generating device and a beam fluence sensor. Furthermore, the accelerator beam intensity control power source is connected to an intensity modulation device, a beam fluence sensor septum and a beam fluence sensor nozzle.

In another general aspect there is provided a method for delivering a longitudinal column of dose rapidly to a depth extrema of a tumor by locating a region of interest of a patient by a position tracking module that includes a registration, verification used in conjunction with a patient motion sensor and a tumor motion sensor to determine the exact location of a target voxel. Additionally, a step of targeting the target voxel within the region of interest includes accessing a treatment plan characterization while providing a prescribed amount of dose to the target voxel, where a scanning routine module determines a prescribed amount of dose for the target voxel in a horizontal index and a single vertical index. Additionally, a step of controlling a power supply for a horizontal magnet and a vertical magnet includes retrieving information from the scanning routine module, that further includes controlling a power supply for an accelerator energy selection that is connected to a beam generating device, where a beam delivery module reads a horizontal strip detector and a vertical strip detector.

Further, the method for delivering a longitudinal column of dose rapidly to the depth extrema of a tumor also includes tracking the region of interest by use of a tumor motion sensor. Furthermore, the method also includes selecting a static delivery or a dynamic delivery to the patient by operating a GUI. Furthermore, the method also includes the steps of populating a database treatment planning system by a beam delivery module and a position and tracking module, delivering a dose prescription to the beam delivery module, measuring a delivery dose from the beam delivery module, incrementing a horizontal index as many times as needed within the region of interest and within the single vertical index, and incrementing the single vertical index as many times as needed with the region of interest.

DETAILED DESCRIPTION

The invention generally relates to a device that is used to treat patients using rapid cycling regarding particle therapy.

The following detailed description is provided to assist the reader in gaining a comprehensive understanding of the methods, apparatuses, and/or systems described herein. Accordingly, various changes, modifications, and equivalents of the systems, apparatuses and/or methods described herein will be suggested to those of ordinary skill in the art. Also, descriptions of well-known functions and constructions may be omitted for increased clarity and conciseness.

In the Summary of the Invention above and in the Detailed Description of the Invention, and the claims below, and in the accompanying drawings, reference is made to particular features (including method steps) of the invention. It is to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with and/or in the context of other particular aspects and embodiments of the invention, and in the invention generally.

Rapid Range Stacking (RRS) is a pencil beam scanning (PBS) method that delivers an entire spread out Bragg peak (SOBP) in order to fill the longitudinal extent of a tumor volume with radiation quickly prior to repositioning the pencil beam in the transverse plane. This enables the 3D tumor volume to be filled with radiation in a single transverse scanning cycle. A SOBP is the superposition of multiple Bragg peaks with each composed of particles at the specified energy required to penetrate the tumor to the longitudinal depth referred to as range. This invention is the method of rapidly stacking multiple pencil beams with particles with range varying from distal to proximal extent of the tumor.

Figure 3:
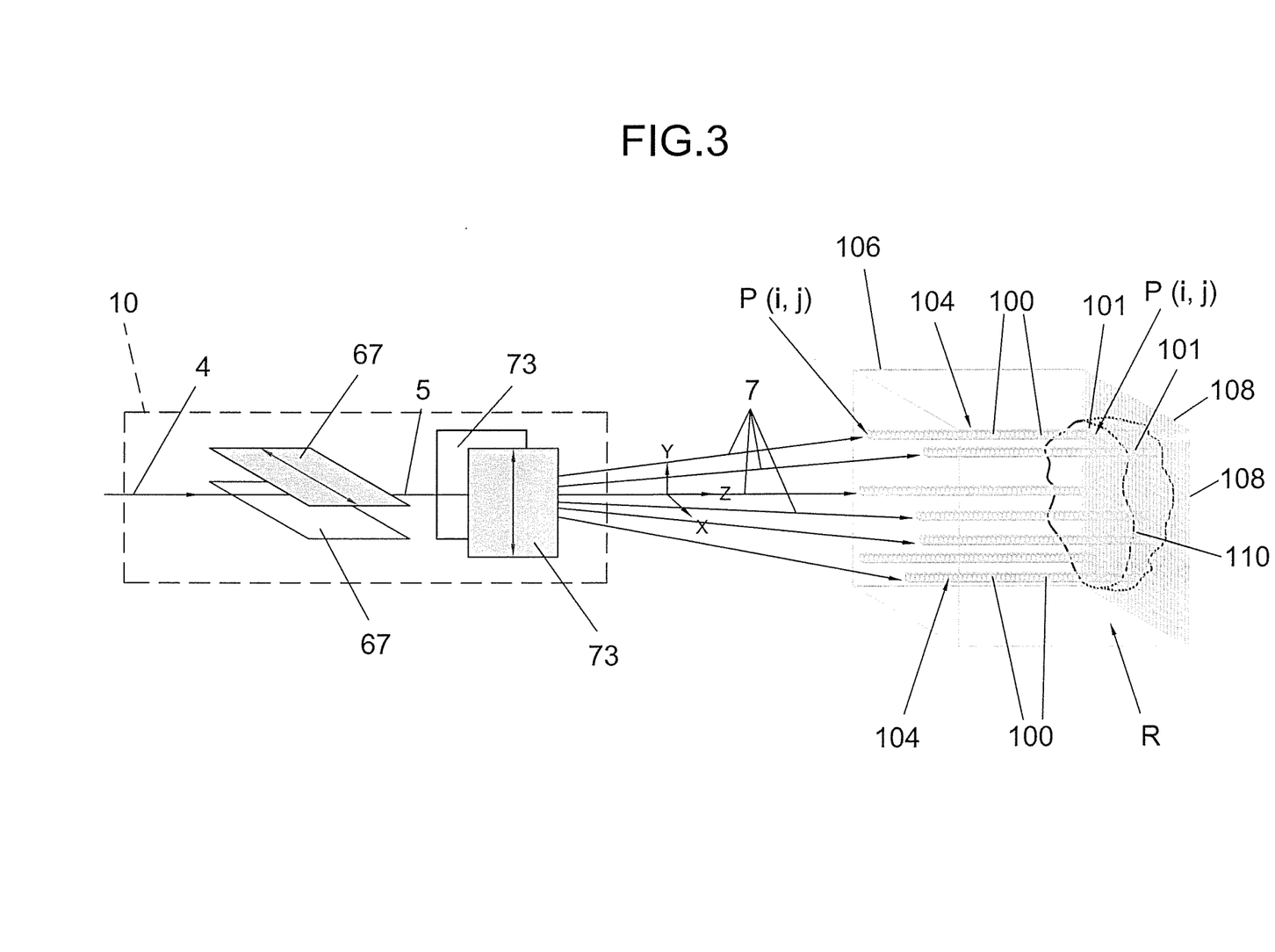
FIG. 3 is an exemplary illustration of the rapid range stacking (RRS) technique for radiating a region of interest.

FIG. 3 is an exemplary illustration showing how the charged particles are deflected by horizontal magnets 67 and vertical magnets 73. Initially, the particle beam 4 is projected through a beam delivery (beam generating) device and first goes through the horizontal magnets 67. As shown in FIG. 3, particle beam 4 represents the particle beam prior to passing through the horizontal magnets 67. The horizontal magnets 67 are used to control the X coordinate position of the particle beam 4. Thereafter, the particle beam 5 travels through the vertical magnets 73 that are used to control the Y coordinate position of the particle beam 5. The Z coordinate position is the direction in which the particle beam is being projected from the beam delivery (beam generating) device 10 into the patient. As shown in FIG. 3, particle beam 5 represents the particle beam after passing through the horizontal magnets 67 but prior to passing through the vertical magnets 73. Specifically, by controlling the strength of each of the vertical magnets 73 and the horizontal magnets 67, the particle beam 7 is being directed to the tumor site of a tumor 110 by using the magnetic flux of the magnets 67 and 73. Further, when looking at the change in energy, an entire stack 104 of voxels 100 is being irradiated by multiple, or a plurality of, particle beams in the tumor 110 rapidly. Particle beam 7 represents the particle beam after passing through both the horizontal magnets 67 and the vertical magnets 73.

Figure 4:
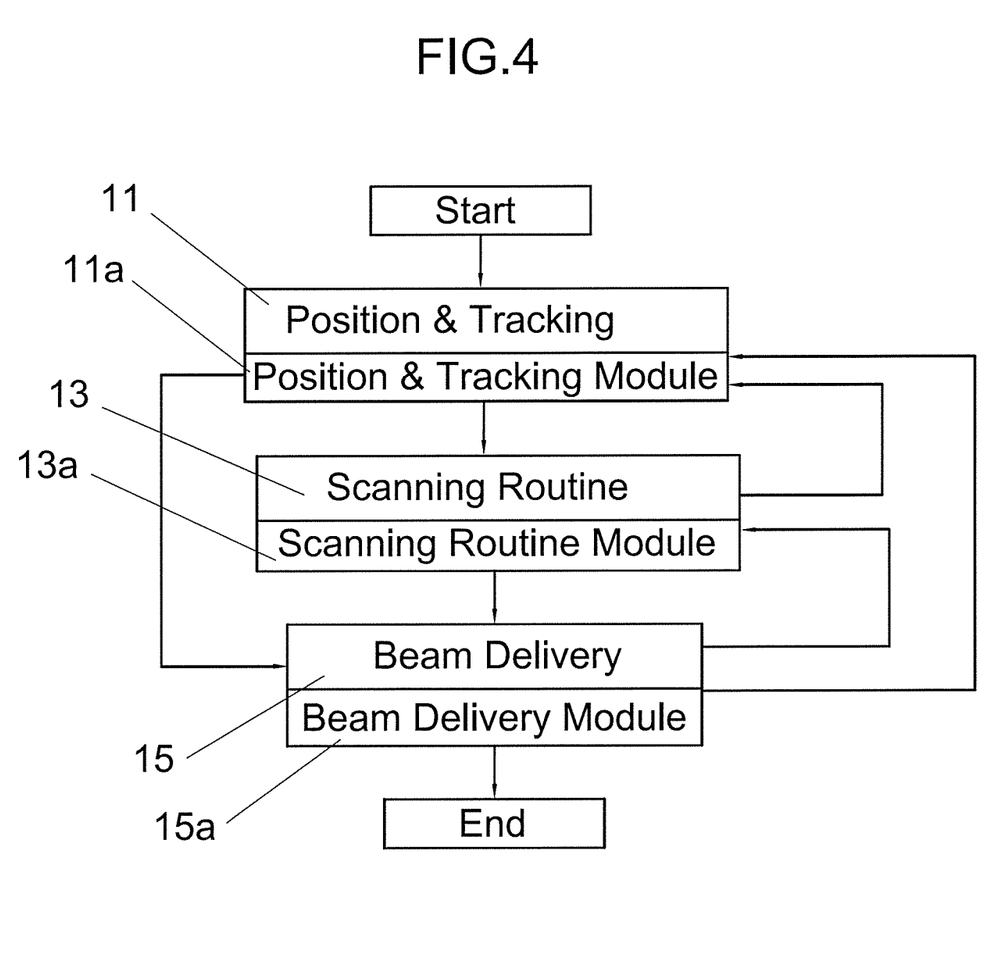
FIG. 4 is a flow chart illustrating the method of operating the rapid range stacking technique.

FIG. 4 is an exemplary block diagram of the treatment routine used by the following system. Initially, the treatment routine begins with patient positioning and tracking 11 by a position and tracking module 11a. Then the treatment routine moves to scanning routine 13 by a scanning routine module 13a, which has multiple options to return back to patient position and tracking 11 or move to beam delivery 15 by a beam delivery module 15a. The scanning routine 13 is used to constantly change the magnetic flux in relation to the tumor position. The beam delivery 15 is used to deliver a wide range of rapid cycling particles to a specific region in the tumor. Beam delivery 15, overall, controls the output of the particles in relation to and with instructions from scanning routine 13. After patient position and tracking 11, scanning routine 13, and beam delivery 15 are complete, then the treatment cycle has ended.

Figure 5:
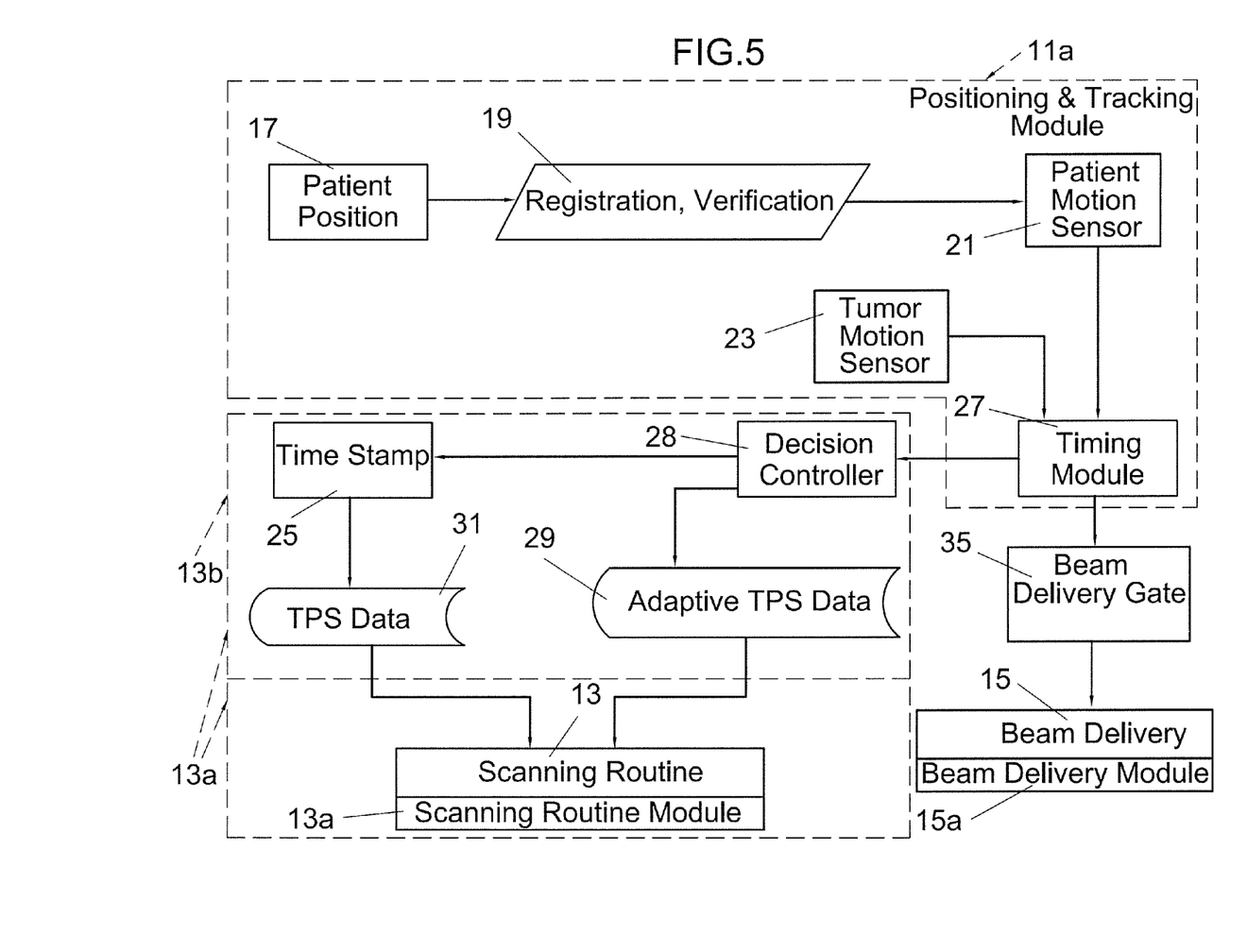
FIG. 5 is an exemplary illustration of the position and tracking steps.

Referring to FIGS. 3-5, FIG. 5 is an exemplary block diagram of the patient position and tracking 11 by the position and tracking module 11*a*, generally indicated in FIG. 5. The patient positioning and tracking 11 is first determined by taking the relative location of the patient, which is in patient position 17. In the patient position 17, you determine the region of interest of the tumor 110. Then, in registration, verification 19, you are verifying the internal target of the patient and are comparing it to the PET, CT, MRI images. Then, you would re-position the patient to correct for any displacement for the patient. The registration, verification 19 is used as an improved method for correcting any undesired regions of interest for treatment. When dealing with the human body, certain regions of the human body can contain constant movement, such as breathing. When trying to determine the region of interest in a lung, there is a patient motion sensor 21. Patient motion sensor 21 is used to determine the contours of the region of interest outside the patient. This method may be done or determined by taking video or a series of sliced images over a period of time. The tumor motion sensor 23 takes the contours of the tumor 110 that is within the patient. The tumor motion sensor 23 is determined by using x-ray beams that take the rhythm of the movement of the tumor and therefore fiducialize the tumor 110 with coordinate marks. These coordinate marks are then used to determine the location of the tumor 110 with respect to time. The image sets that are taken by the tumor motion sensor 23 are correlated to the image sets that are located in the registration, verification 19 of the patient. Therefore, after correlation, the tumor motion sensor 23 will provide an X-coordinate position, a Y-coordinate position, and a Z-coordinate position time-position for a specific region within the tumor 110. The time module 27 takes all this information for confirmation and then delivers this confirmation to the beam delivery gate 35. Timing module 27 is then connected to a decision controller 28, which is manually controlled by a GUI user to choose one of two tracking modes that utilize either static delivery or a dynamic delivery. Static delivery is operated by a static timing for TPS data 31 and dynamic delivery is operated by an adaptive TPS data 29. When taking the static timing for TPS data 31, the static time stamp 25 takes the specific time and applies a certain amount of dose D at that position. The static timing for TPS data 31 contains a library of information regarding time and specific positions of the tumor 110. Basically, static time stamp 25 is waiting for the tumor 110 to be in a specific position relative to the time, which then provides information to beam delivery gate 35 and associated beam delivery module 15*a* to control a beam generating device 79 (FIG. 7) of the beam delivery device 10 for beam delivery 15. FIG. 5 also generally indicates a database treatment planning system 13*a*, associated with the scanning routine module 13*a*, that is associated with the beam delivery module 15*a* and the position and tracking module 11*a*. The scanning routine module 13*a* retrieves from the database treatment planning system 13*b* a dose prescription, a position location, a position time for a specific voxel, and a flag for dose delivery. The benefit of static timing for TPS data 31 is that you are able to irradiate/provide dose to a region of interest at a specific time. For example, if a tumor is moving within a certain constant frequency and that frequency of movement is a +5 cm/−5 cm indicating a total of 10 cm movement, by using the patient motion sensor 21 and the tumor motion sensor 23, static time stamp 25 for TPS data 31 will indicate its precise time within the frequency and location of the tumor 110 to be radiated, therefore so as not to irradiate/provide dose areas outside the region of interest. The verification is done in the TPS data 31, which then determines if there is timing information for the region of interest. This is different from the dynamic delivery by the adaptive TPS data 29. The adaptive TPS data 29, when initiated, takes constant information from the patient motion sensor 21 and the tumor motion sensor 23 and uses this information by taking data points Epromixal (t), Edistial(t), Xo(t), Xn(t), Yo(t), and Ym(t). Adaptive TPS data 29 is used to provide a rapid dose D at multiple frequency positions for a stack of 104 of voxels 100 relative to time. The adaptive TPS data 29, unlike the static time stamp 25 for TPS data, has multiple information points of time and position regarding the region of interest. In comparison, the static time stamp 25 for TPS data 31 only has one specific position relative to time for the region of interest. Thus the adaptive TPS data 29 allows for multiple deliveries of dose D of a moving region of interest in a constant frequency. For example, if a tumor is located near the lung and there is the patient motion sensor 21 and the tumor motion sensor 23, that information therefrom can be used to verify specific points of the region of interest and provide multiple dose delivery of the region of interest within a single frequency, thus, providing quicker dose treatment to the patient. Further, the adaptive TPS data 29 also indicates that if the region of interest were to move, the system will compensate by providing a dose at a close distance or to a further distance relative to the tumor 110. Adaptive treatment requires various prescriptions corresponding to different tumor positions specified in the energy deposition array 106 energy (x, dx, y, dy, z, dz, particle, t). This energy deposition array 106 energy specifies the prescribed dose for the given particles at each position and step in time. The information is then sent to the scanning routine 13.

Next, timing module 27 sends information to the beam delivery gate 35. The beam delivery gate 35 is used to communicate dose information at a specific time. The beam delivery gate 35 is used to synchronize the delivery of the beam with the moment in time and communicates to the beam delivery 15 as to when to turn the beam on or off.

Figure 6:
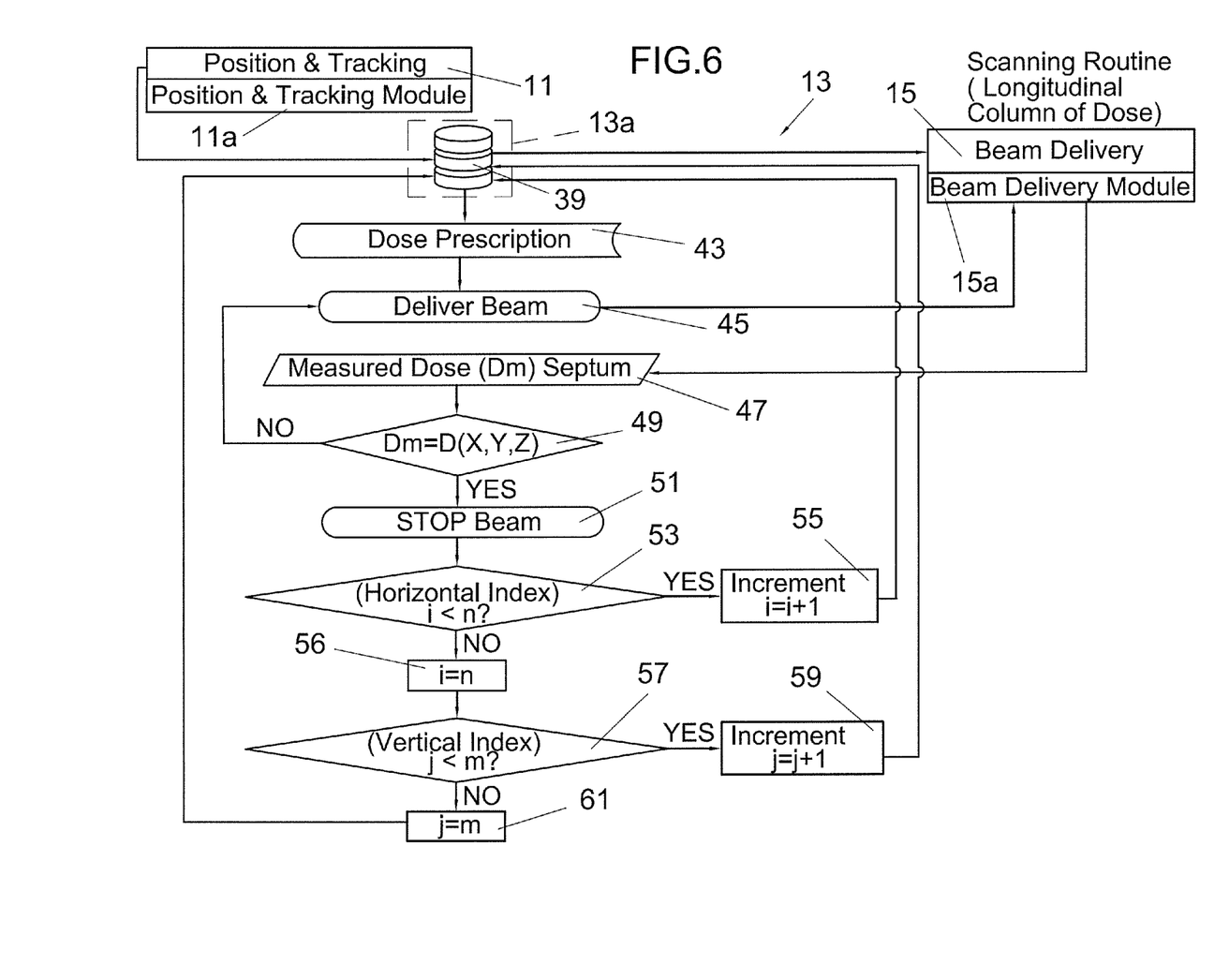
FIG. 6 is an exemplary illustration of the scanning routine of the RRS technique.

Referring to FIG. 6, as well as to FIGS. 3, 4, 5 and 7, FIG. 6 is an exemplary block diagram of the scanning routine 13 by the scanning routine module 13*a* of FIG. 4. The scanning routine 13 is to verify that rapidly stacking multiple pencil beams are delivered to a specific coordinate prior to moving to another location. The lookup TPS data 39 is a treatment plan database associated with the database treatment planning system 13*b* of the scanning routine module 13*a*, generally indicated in FIG. 6, that contains data for all verified points of the region of interest. The lookup TPS data 39 contains the dose prescription 43 or the energy intensity that will be used for each specific voxel 100. The system takes this patient specific information, and determines the amount of dose D each voxel 100 will receive and sets parameters for the beam delivery 15 for the beam to be delivered at 45 deliver beam to one or more target voxels 101 at one or more corresponding data points 108 at a position "i" of a horizontal index (X) and at a position "j" of a vertical index (Y) at a corresponding depth (Z) for one or more stacks 104 of voxels 100 of the energy deposition array 106 for the region of interest R, such as including the tumor 110. The information contains the amount of energy and intensity that is used for each voxel 100. Then, the dose prescription 43 initiates deliver beam 45, which then selects a specific energy level. This energy level is very important to determine, since in ion therapy the particles have an inverse peak energy point, the specific distance of the tumor 110 regarding the rise in energy delivery. The deliver beam 45 can be initiated by starting with a high energy or a low energy level, which means that the treatment to the region of interest R, such as including the tumor 110, is furthest from the beam treatment or closest to the beam treatment. The deliver beam 45 of the beam delivery device 10 also indicates the energy for the horizontal magnets 67 and the vertical magnets 73 used in beam delivery 15. The beam energy is continuously indexed between extrema of the tumor 110, as the system measures at 47 the corresponding dose D at a corresponding depth (Z) being delivered from the beam generating device 79 of the beam delivery device 10 to each corresponding target voxel 101. The measured dose Dm at measured dose septum 47 is used by the delivery system of the beam delivery device 10 to control the intensity at each energy to generate a uniform SOBP that is delivered to the patient. Further, the measured dose at measured dose septum 47 at the beam generating device (example: at extraction septum) is used to determine the integrated dose for that specific voxel 100, such as for a specific target voxel 101. The measured dose at 47 at extraction septum takes delivery dose infolination and stores it for recordation purposes. Next, it is determined by the beam delivery device 10 at 49 if the measured dose Dm is equal to the dose prescription for each corresponding target voxel 101 at a corresponding data point 108 at an associated depth (Dm=D(X,Y,Z)) in a stack 104 of voxels 100 and a command loop of the beam delivery device 10 determines if the measured dose at 47 is equal to/reached the amount of dose required for that target voxel 101 at 49. If the measured dose has not reached the dose prescription, the command operator of the beam delivery device 10 continues beam deliver at 45 for beam delivery at 15 and then receives a measured dose at septum at 47 from beam delivery at 15 to yet again determine if a measured dose is equal to a prescription dose for that specific voxel 100 at 49. When, it is determined at 49 that the measured dose at 47 for each target voxel 101 at each corresponding data point 108 (X,Y,Z) in a stack 104 of voxels 100 at a horizontal index (X) is equal to its prescription dose, such that it is determined a corresponding dose prescription for the target voxels 101 at one or more corresponding data points 108 in a stack 104 of voxels 100 at a position P (i,j) has been reached, (Dm=D(X,Y,Z)), the system stops beam delivery at stop beam at 51. Afterwards, the system of the beam delivery device 10 determines at 53 if "i" is less than a total number "n" positions of horizontal indexes (X) corresponding to a single vertical index (Y) and, if so, increments the horizontal index (X) from a position "i" to another position "i=i+1" at 55 for the single vertical index (Y) and delivers the corresponding dose prescription to target voxels 101 at corresponding data points 108 in a stack 104 of voxels 100 at position "i=i+1", as described, for a corresponding stack 104 of voxels 100 at the incremented position "i=i+1"on a same single vertical index (Y) in the energy deposition array 106 and returns to lookup TPS data 39 to initiate all the steps 43, 45, 47, 49, 51 and 53, and depending on the determination at 53, selectively initiates step 55 or step 56, as herein described. By incrementing a position "i" of horizontal index (X) at 53 by+1, the system of the beam delivery device 10 has to look up all treatment planning system data for the new specific voxels 100 and then again treat the specific voxels 100 with the following steps in dose prescription at 43, and sends the information to deliver beam at 45 for beam delivery at 15, measures a measured dose Dm at 47 from beam delivery at 15 and then determines at 49 whether a dose prescription equals to a corresponding measured dose prescription for the target voxels 101 in a corresponding stack 104 of voxels 100 at the incremented horizontal index (X) for a corresponding single vertical index (Y), Dm=D (X,Y,Z); and, if so, stops beam delivery at stop beam at 51. The incrementing of the horizontal index (X) of the corresponding single vertical index (Y) continues at 55 and the dose prescription delivery continues for target voxels 101 in a corresponding stack 104 of voxels 100 until the horizontal index (X) of the corresponding single vertical index (Y) has been incremented from a position "i" at 53, and a dose prescription has been provided, for the total number of positions "n" of horizontal indexes (X) corresponding to a single vertical index (Y), such that "i" is equal to "n" (i=n) at 56. If so, thereafter, the system then determines at 57 from a position "j" of the single vertical index (Y) if "j" is less than a total number of positions "m" of vertical indexes (Y) in the energy deposition array 106 for delivery of a dose prescription to target voxels 101 in a corresponding stack 104 of voxels 100. If it is determined at 57 that "j" is less than "m", ("j<m"), at 59 a position "j" of the single vertical index (Y) is incremented by+1 to a position "j=j+1" of the incremented vertical index (Y), and yet again, returns to lookup TPS data 39 to initiate all the steps 43, 45, 47, 49, 51 and 53, as well as selectively initiates steps 55 or 56, as herein described, for delivering a corresponding dose prescription to each target voxel 101 for a corresponding stack 104 of voxels 100 for the horizontal indexes (X) associated with the corresponding incremented single vertical index (Y). The incrementing of a position "j" of the vertical index (Y) continues at 59 until it is determined at 57 that a dose prescription has been provided to the target voxels 101 in corresponding stacks 104 of voxels 100 for the total number of positions "m" of vertical indexes (Y) in the energy deposition array 106 by it being determined that "j" is not less "m". If at 57 it is determined that "j" is not less than "m", then at 61 "j" is now equal to "m" (j=m), and a corresponding dose prescription, as described, has been provided for the total number positions "m" of vertical indexes (Y) in the energy deposition array 106 and, therefore, at 61, where j=m, a corresponding dose prescription has been provided to all of the target voxels 101 in the energy deposition array 106 such that j=m and i=n and the process returns from 61 to lookup TPS data 39 to end. This process of rapidly scanning energy to deliver a uniform Spread Out Bragg Peak (SOBP) in a single transverse X-Y scan has the efficiency of reducing latent scanning periods used to deliver a dose. The system delivers the dose as precisely as possible through the generation of a uniform Spread Out Bragg Peak in a single beam generation cycle. Instead of delivery of an individual dose in a single X-Y plane, the beam delivery device 10 is delivering the dose to a stack 104 of voxels 100 in the z-coordinate rapidly. When, all be vertical indexes (Y) have been incremented, such that j=m at 61, the system has scanned and delivered the dose in stacks to the region of interest R.

Figure 7:
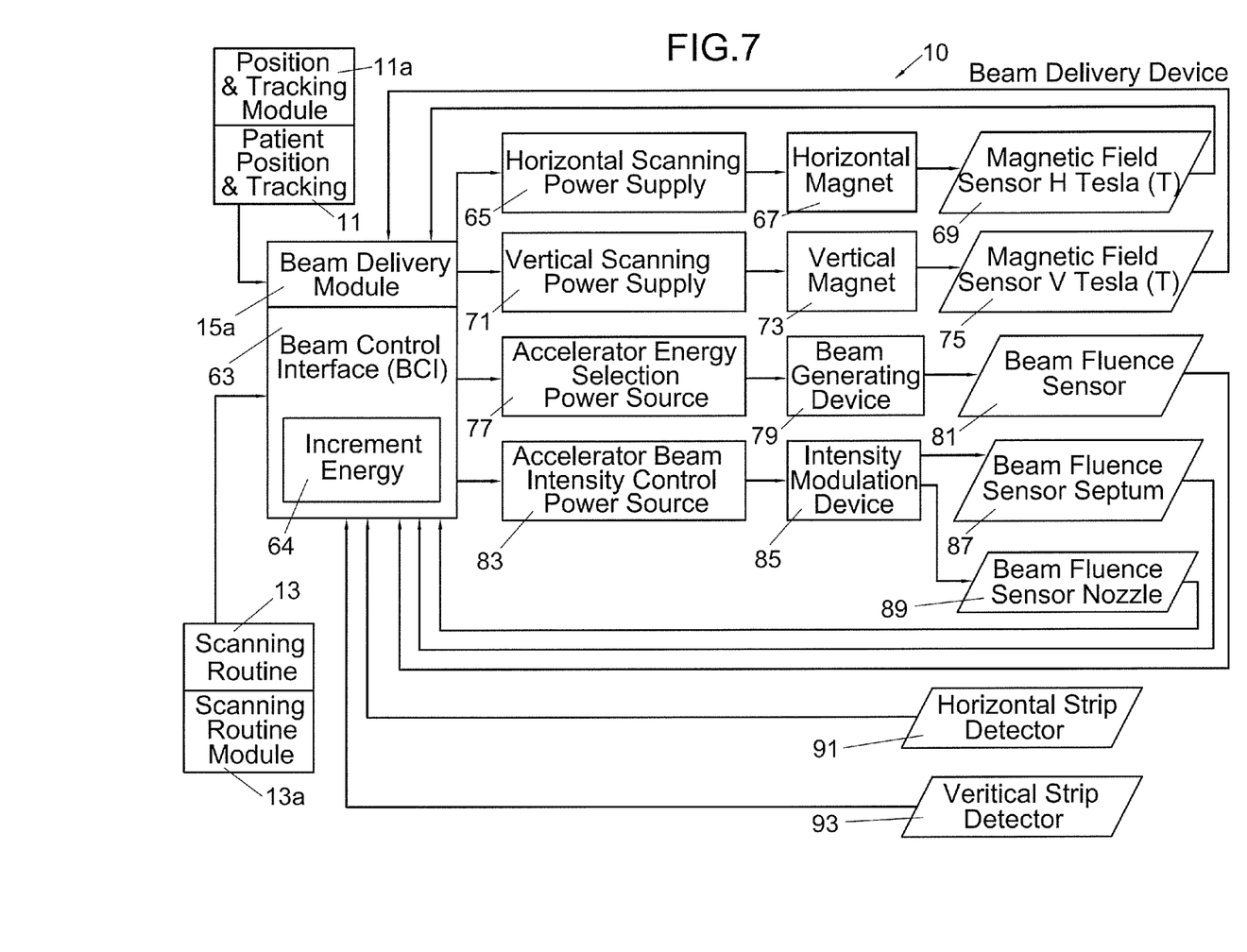
FIG. 7 is an exemplary illustration of the beam delivery process of the RRS technique.

Referring to FIG. 7, as well as to FIGS. 3, 4, 5 and 6, FIG. 7 is an exemplary block diagram of the beam delivery device 10 associated with the scanning routine 13 by the scanning routine module 13a of FIG. 4. The beam delivery 15 by the beam delivery module 15a is controlled by a beam control interface 63 associated with the beam delivery module 15a. The beam control interface 63 also has incremental energy distribution information that is received from the scanning routine 13. The main purpose of the beam control interface 63 is to allow a universal control module that operates the delivery of dose while taking information from the patient position tracking 11 and the scanning routine 13. By creating one central control interface, such as the beam control interface 63, the system operates in a static manner, which means that all major control functions are operated in a single control module when delivering dose to the patient and, therefore, reducing motor control interference and processing latency. Further, the beam delivery device 10 including the beam control module 15a of the beam delivery 15 controls all parameters that are referred to by the dose prescription 43 within the scanning routine 13. The scanning routine 13 provides command information to the beam control interface 63, which then controls the increment energy 64. Depending upon the information provided from the scanning routine 13, the beam control interface 63 initially instructs the horizontal scanning power supply 65. The horizontal scanning power supply 65 is used to control the polarity and intensity of the horizontal magnets 67 by controlling electric current that affects the magnetic flux which then changes the magnetic field sensor 69. The magnetic field sensor 69 is used to verify beam deflection and beam position. The magnetic field sensor 69 provides verification data to the beam control interface 63 to increase or decrease horizontal scanning power supply 65. When the magnetic field sensor 69 provides the correct horizontal position, the beam control interface 63 thereafter initiates accelerator energy synchronization of the acceleration energy selection power source 77. The accelerator energy selection power source 77 is used to control the energy of the delivery and the beam generating device 79 is used to synchronize the beam energy index between extrema of the tumor 110. The beam energy index is specified by the Bragg peak width from minimum to maximum penetration depth. The beam generating device 79 synchronizes the intensity modulation device 85 before the particle beam is delivered to the treatment device. The particle beam is measured with a beam fluence sensor 81 located in an energy sensitive position; and, thereafter, the particle beam travels from the treatment device to the patient's region of interest. The beam fluence sensor 81 is used to measure the amount of radiation as energy is changing and is recorded into the beam control interface 63. The beam control interface 63 will then provide this information to the scanning routine 13 to determine if that specific voxel has reached its prescription dose level. When the voxel has received its prescription dose level as verified in the scanning routine 13 by the scanning routine module 13a, the beam control interface 63 then, again, in a nested loop, changes the horizontal scanning power supply 65 which then controls the horizontal magnets 67 which then is read by the magnetic field sensor H 69, as a first magnetic field sensor, that is directed to the next position in the horizontal index at 53 within the region of interest R for treatment. When the scanning routine 13 by the scanning routine module 13a has indicated that all horizontal voxel's have been treated at a corresponding single vertical index (Y), the beam control interface 63 then will instruct a vertical scanning power supply 71, which then controls the vertical magnets 73, which then is read by a magnetic field sensor V 75, as a second magnetic field sensor. Once the vertical magnets 73 are set in a precise field strength for a corresponding single vertical index (Y), the beam control interface 63 will then operate the horizontal scanning power supply 65, the horizontal magnets 67 and will read the magnetic field sensor H 69 which will then operate the accelerator energy selection power source 77 to deliver the dose in the beam generating device 79 and verify this information in the beam fluence sensor 81. The benefit of this nested loop is that a full column of dose is delivered filling multiple voxels with multiple energy levels rapidly. The intensity of each energy level is controlled by the accelerator energy selection power source 77 and incremented for each energy level. Traditional pencil beam scanning delivers 2D transverse slices of dose to the tumor 110 one energy level piecewise layer by layer. The beam control interface 63 can also operate an accelerator beam intensity control power source 83 which is used to control the intensity of the delivered beam in association with an intensity modulation device 85 as the beam energy is continuously indexed between extrema of the tumor 110. This intensity control is specified to produce a uniform SOBP for each penetration depth. The intensity modulation device 85 delivers the particle beam to the treatment device and the particle beam is measured in the treatment device with the beam fluence sensor 81; and thereafter, the particle beam travels from the treatment device which contains a beam fluence sensor septum 87 and a beam fluence sensor nozzle 89 to the patient's region of interest. The beam fluence sensor septum 87 is used to measure the amount of radiation the patient has received and is recorded into the beam control interface 63. The SOBP is generated by the summation of intensity modulated Bragg peaks from $Z_o$ to $Z_n$ where the index step is specified by the Bragg width at each energy as in the following relation (1):

$$SOBP(Z_o:Z_n)=SUM(C_o*Z_o:C_n*Z_n). \tag{1}$$

The intensity is modulated from $C_o$ to $C_o$ where the maximum intensity is associated with the beam with the highest energy within the SOBP. A horizontal strip detector 91 provides feedback to the beam control interface 63 to verify a correct horizontal scan position. A vertical strip detector 93 additionally provides feedback to the beam control interface 63 to verify a correct vertical scan position.

All the features disclosed in this specification (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

The invention claimed is:

1. An apparatus for delivering a longitudinal column of dose to a region of interest of a patient for treatment, comprising:
 a position and tracking module to determine a patient position and to locate a region of interest for treatment, the position and tracking module determining a respective position location of one or more target voxels in one or more stacks of voxels in said region of interest;
 a scanning routine module to target each target voxel of said one or more target voxels in an energy deposition array within said region of interest to selectively provide a dose prescription to each said target voxel of said one or more target voxels, each said target voxel of said one or more target voxels being respectively located at a respective data point in said energy deposition array and being respectively located in a stack of voxels of the one or more stacks of voxels in said energy deposition array in said region of interest, each respective said data point being respectively located at a horizontal index of one or more horizontal indexes and at a vertical index of one or more vertical indexes at an associated depth in said energy deposition array, the scanning routine module determining respectively, for each vertical index of the one or more vertical indexes in said energy deposition array in said region of interest, an amount of a respective said dose prescription for each said target voxel of said one or more target voxels, each said target voxel being respectively located at a respective said data point in said energy deposition array and at a horizontal index of the one or more horizontal indexes and at a vertical index of the one or more vertical indexes in said energy deposition array; and a beam delivery device to deliver to each said target voxel in a said stack of voxels of the one or more stacks of voxels in said energy deposition array in said region of interest a longitudinal column of dose of ion particles in a plurality of beams, each of the plurality of beams in a respective said longitudinal column of dose being respectively delivered to said stack of voxels of the one or more stacks of voxels having an energy intensity of a respective determined said dose prescription for a respective said target voxel of said one or more target voxels at a respective said data point in said stack of voxels of the one or more stacks of voxels in said energy deposition array, the beam delivery device delivering one respective said longitudinal column of dose to one stack of voxels of the one or more stacks of voxels respectively located at one horizontal index of the one or more horizontal indexes and at one vertical index of the one or more vertical indexes in said energy deposition array before incrementing to another stack of voxels of the one or more stacks of voxels respectively located at the one vertical index and at another horizontal index of the one or more horizontal indexes or before incrementing to another stack of voxels of the one or more stacks of voxels respectively located at another vertical index of the one or more vertical indexes and at the one or a said another horizontal index of the one or more horizontal indexes in said energy deposition array to deliver another respective said longitudinal column of dose to a said another stack of voxels of the one or more stacks of voxels respectively located at the one or a said another horizontal index of the one or more horizontal indexes and at the one or a said another vertical index of the one or more vertical indexes in said energy deposition array within said region of interest.

2. The apparatus according to claim 1, wherein said position and tracking module further comprises:
a tumor motion sensor to determine a contour of a tumor and a patient motion sensor to determine a contour outside of a patient for said region of interest, wherein said tumor motion sensor tracks said region of interest.

3. The apparatus according to claim 2, wherein said position and tracking module further comprises:
a timing module to provide timing information is connected to a decision controller, said decision controller to select a static delivery or a dynamic delivery for the one or a said another respective said longitudinal column of dose,
wherein said static delivery includes a static time stamp for a position relative to time to provide each dose to said region of interest at an associated time and uses treatment planning system data used by said scanning routine module, and
wherein said dynamic delivery includes adaptive treatment planning data to provide for respective doses at multiple positions relative to time used by said scanning routine module to provide a respective said dose prescription for each said target voxel of said one or more target voxels in said energy deposition array within said region of interest.

4. The apparatus according to claim 2, wherein said position and tracking module further comprises:
a timing module to provide timing information is connected to a beam delivery gate that is used by a beam delivery module to control the beam delivery device to respectively deliver the ion particles in the one or a said another respective said longitudinal column of dose to each said target voxel in the one or a said another stack of voxels of the one or more stacks of voxels within said region of interest.

5. The apparatus according to claim 1, wherein said scanning routine module further comprises:
a treatment plan database for data communication with a beam delivery module and said position and tracking module, said beam delivery module controlling said beam delivery device to deliver the ion particles to each said target voxel of said one or more target voxels respectively located in the one or a said another stack of voxels respectively located at the one or a said another horizontal index of the one or more horizontal indexes and at the one or a said another vertical index of the one or more vertical indexes in said energy deposition array within said region of interest.

6. The apparatus according to claim 5, wherein:
said scanning routine module retrieves from said treatment plan database a respective said dose prescription, a position location of a respective said data point, a position time for dose delivery for a respective said target voxel of said one or more target voxels in said region of interest, and a flag for the dose delivery to deliver the ion particles of a respective determined said dose prescription to each said target voxel in the one or a said another stack of voxels respectively located at the one or a said another horizontal index of the one or more horizontal indexes and at the one or a said another vertical index of the one or more vertical indexes in said energy deposition array within said region of interest.

7. The apparatus according to claim 6, wherein:
said scanning routine module initiates a beam delivery to said beam delivery module to initiate delivery of a respective determined said dose prescription to each said target voxel of said one or more target voxels respectively located in the one or a said another stack of voxels respectively located at the one or a said another horizontal index of the one or more horizontal indexes and at the one or a said another vertical index of the one or more vertical indexes in said energy deposition array within said region of interest and to trigger a stop to the beam delivery.

8. The apparatus according to claim 7, wherein:
the plurality of beams of the ion particles respectively delivered to each said target voxel of said one or more target voxels respectively located in the one or a said another stack of voxels respectively located at the one or a said another horizontal index of the one or more horizontal indexes and at the one or a said another vertical index of the one or more vertical indexes in said energy deposition array within said region of interest include a spread out Bragg peak generated by a summation of intensity modulated Bragg peaks.

9. The apparatus according to claim 1, wherein:
the scanning routine module determines a respective determined said dose prescription for delivery to each said target voxel of said one or more target voxels respectively located at a respective said data point in the one stack of voxels of the one or more stacks of voxels respectively located at the one horizontal index of the one or more horizontal indexes and at the one vertical index of the one or more vertical indexes and then determines a respective determined said dose prescription for delivery to each said target voxel of said one or more target voxels in a said another or a next said another stack of voxels of the one or more stacks of voxels respectively located at a said another or a next said another horizontal index of the one or more horizontal indexes and at the one vertical index of the one or more vertical indexes by incrementing from the one horizontal index to a said another or a next said another horizontal index on the one vertical index in said energy deposition array until a respective determined said dose prescription for each said target voxel of said one or more target voxels respectively located at the one, a said another or a next said another horizontal index of the one or more horizontal indexes located at the one vertical index of the one or more vertical indexes has been determined for delivery and then incrementing to a said another stack of voxels of the one or more stacks of voxels respectively located at a said another or a next said another vertical index of the one or more vertical indexes in said energy deposition array and determining a respective determined said dose prescription for delivery to each said target voxel of said one or more target voxels located at a said respective data point in a said another stack of voxels of the one or more stack of voxels respectively located at the one, a said another or a next said another horizontal index of the one or more horizontal indexes located at a said another or a next said another vertical index of the one or more vertical indexes in said energy deposition array, the incrementing continuing until a respective determined said dose prescription has been determined for delivery to each said target voxel of said one or more target voxels respectively located at a respective said data point in said energy deposition array within said region of interest.

10. The apparatus according to claim 1, further comprising:
a beam delivery module including a beam control interface connected to a horizontal power supply for a horizontal magnet and a vertical power supply for a vertical magnet to respectively control beam delivery to each said target voxel of said one or more target voxels, each said target voxel being respectively located at a respective said data point in said energy deposition array and in a stack of voxels of the one or more stacks of voxels and respectively located at the one or a said another vertical index of the one or more vertical indexes and at the one or a said another horizontal index of the one or more horizontal indexes in said energy deposition array within said region of interest.

11. The apparatus according to claim 10, wherein:
the beam control interface is connected to an accelerator energy selection power source and an accelerator beam intensity control power source to respectively control the beam delivery to each said target voxel of said one or more target voxels located at a respective said data point in said energy deposition array within said region of interest.

12. The apparatus according to claim 10, wherein:
said horizontal power supply is connected to said horizontal magnet and a first magnetic field sensor to respectively control a horizontal coordinate position of the plurality of beams for the beam delivery to each said target voxel of said one or more target voxels located at a respective said data point in said energy deposition array within said region of interest.

13. The apparatus according to claim 12, wherein:
said vertical power supply is connected to said vertical magnet and a second magnetic field sensor to respectively control a vertical coordinate position of the plurality of beams for the beam delivery to each said target voxel of said one or more target voxels located at a respective said data point in said energy deposition array within said region of interest.

14. The apparatus according to claim 13, wherein:
the beam control interface is connected to an accelerator energy selection power source and an accelerator beam intensity control power source to respectively control the beam delivery to each said target voxel of said one or more target voxels located at a respective said data point in said energy deposition array within said region of interest,
wherein said accelerator energy selection power source is connected to a beam generating device and a beam fluence sensor for control of the beam delivery.

15. The apparatus according to claim 14, wherein:
said accelerator beam intensity control power source is connected to an intensity modulation device, a beam fluence sensor septum and a beam fluence sensor nozzle for control of the beam delivery.

16. A method for delivering a longitudinal column of dose to a region of interest of a patient for treatment, comprising the steps of:
locating a region of interest for treatment and determining each respective position location of target voxels in said region of interest;
targeting said target voxels within said region of interest for treatment, each target voxel of said target voxels being associated with a stack of voxels of one or more stacks of voxels in said region of interest, and each said target voxel of said target voxels having a respective data point in an energy deposition array in said region of interest, each respective said data point being located at an X coordinate position of a horizontal index of one or more horizontal indexes in said energy deposition array, at a Y coordinate position of a vertical index of one or more vertical indexes in said energy deposition array and at a Z coordinate position of an associated depth in said energy deposition array;
determining for the one or more vertical indexes in said energy deposition array in said region of interest an amount of a respective dose prescription for each said target voxel of said target voxels respectively located in the one or more stacks of voxels respectively located at a horizontal index of the one or more horizontal indexes and at a vertical index of the one or more vertical indexes in said energy deposition array within said region of interest; and
delivering to a said stack of voxels of the one or more stacks of voxels that includes one or more of said target voxels located in said energy deposition array in said region of interest a longitudinal column of dose of ion particles in a plurality of beams, each of the plurality of beams for beam delivery respectively having an energy intensity corresponding to a respective determined said dose prescription for a respective said target voxel in said stack of voxels of the one or more stacks of voxels at a respective said data point in said energy deposition array, wherein a respective said longitudinal column of dose is delivered to one stack of voxels of the one or more stacks of voxels respectively located at one horizontal index of the one or more horizontal indexes and at one vertical index of the one or more vertical indexes before incrementing to a location of another stack of voxels of the one or more stacks of voxels respectively located at the one vertical index and at another horizontal index of the one or more horizontal indexes or before incrementing to a location of another stack of voxels of the one or more stacks of voxels respectively located at another vertical index of the one or more vertical indexes and at the one or another horizontal index of the one or more horizontal indexes in said energy deposition array to deliver another respective said longitudinal column of dose to a said another stack of voxels of the one or more stacks of voxels respectively located at the one or a said another horizontal index of the one or more horizontal indexes and at the one or a said another vertical index of the one or more vertical indexes in said energy deposition array within said region of interest, and continuing the incrementing until a said another respective said longitudinal column of dose has been delivered to each said another stack of voxels of the one or more stacks of voxels in said energy deposition array within said region of interest.

17. The method according to claim 16, further comprising the steps of:
tracking said region of interest to determine a contour of a tumor associated with said region of interest by use of a tumor motion sensor for control of the beam delivery; and
determining a contour outside of a patient for said region of interest by a patient motion sensor for control of the beam delivery.

18. The method according to claim 16, further comprising the step of:
selecting for the beam delivery a static delivery or a dynamic delivery for each respective said longitudinal column of dose of the ion particles in the plurality of beams respectively delivered to the one or a said another stack of voxels of the one or more stacks of voxels in said energy deposition array within said region of interest.

19. The method according to claim 16, wherein:
delivering to the one or a said another stack of voxels of the one or more stacks of voxels a respective said longitudinal column of dose of the ion particles in the plurality of beams includes delivering a spread out Bragg peak.

20. An apparatus for delivering a longitudinal column of dose to a region of interest of a patient for treatment, comprising:
a position and tracking module to locate a region of interest for treatment and to determine a respective position location of target voxels in said region of interest;
a scanning routine module to selectively target said target voxels in an energy deposition array in said region of interest for treatment, each target voxel of said target voxels having a respective data point in said energy deposition array and being located in a stack of voxels of one or more stacks of voxels in said energy deposition array in said region of interest, each respective said data point being located at an X coordinate position of a horizontal index of one or more horizontal indexes in said energy deposition array, at a Y coordinate position of a vertical index of one or more vertical indexes in said energy deposition array and at a Z coordinate position of an associated depth in said energy deposition array, said scanning routine module determining an amount of a respective dose prescription for each said target voxel of said target voxels respectively located in a said stack of voxels of the one or more stacks of voxels and at a respective said data point in said energy deposition array; and
a beam delivery device to selectively deliver to a said stack of voxels of the one or more stacks of voxels that includes one or more of said target voxels in said energy deposition array in said region of interest a longitudinal column of dose of ion particles in a plurality of beams, each of the plurality of beams in a respective said longitudinal column of dose being respectively delivered to said stack of voxels of the one or more stacks of voxels having an energy intensity of a respective determined said dose prescription for a respective said target voxel of said one or more target voxels in said stack of voxels at a respective said data point in said energy deposition array, the beam delivery device delivering a respective said longitudinal column of dose to one stack of voxels of the one or more stacks of voxels respectively located at one horizontal index of the one or more horizontal indexes and at one vertical index of the one or more vertical indexes before incrementing to another stack of voxels of the one or more stacks of voxels respectively located at the one vertical index and at another horizontal index of the one or more horizontal indexes or before incrementing to another stack of voxels of the one or more stacks of voxels respectively located at another vertical index of the one or more vertical indexes and at the one or a said another horizontal index of the one or more horizontal indexes in said energy deposition array to deliver another respective said longitudinal column of dose to a said another stack of voxels of the one or more stacks of voxels respectively located at the one or a said another horizontal index of the one or more horizontal indexes and at the one or a said another vertical index of the one or more vertical indexes in said energy deposition array within said region of interest.

* * * * *

UNITED STATES PATENT AND TRADEMARK OFFICE
CERTIFICATE OF CORRECTION

PATENT NO. : 9,597,529 B2  
APPLICATION NO. : 13/604415  
DATED : March 21, 2017  
INVENTOR(S) : Joseph Lidestri It is certified that error appears in the above-identified patent and that said Letters Patent is hereby corrected as shown below:

In the Specification

1. Column 7, in Line 35, "time module 27" should read --timing module 27--; and, in Lines 53-54, "database treatment planning system 13a" should read --database treatment planning system 13b--.

2. Column 8, in Lines 11-12, "stack of 104 of voxels 100" should read --stack 104 of voxels 100--.

3. Column 9, in Line 23, "infolination" should read --information--; and, in Lines 33-34, "beam deliver at 45" should read --deliver beam at 45--.

4. Column 11, in Line 8, "beam control module 15a" should read --beam delivery module 15a--.

5. Column 12, in Line 28, "The intensity is modulated from Co to Co" should read --The intensity is modulated from Co to Cn--.

Signed and Sealed this  
Ninth Day of May, 2017

Michelle K. Lee  
*Director of the United States Patent and Trademark Office*